United States Patent [19]

Wilkinson

[11] 3,954,739

[45] May 4, 1976

[54] BIOLOGICAL REAGENT

[75] Inventor: Samuel Wilkinson, Beckenham, England

[73] Assignee: Burroughs Wellcome Co., Research Triangle Park, N.C.

[22] Filed: June 21, 1973

[21] Appl. No.: 372,035

[52] U.S. Cl. ................. 260/239.57; 260/112.5 R; 250/303; 424/1; 23/252 R
[51] Int. Cl.² ........................................ C07J 19/00
[58] Field of Search .................. 260/112.5, 239.57

[56] References Cited
UNITED STATES PATENTS

| | | | |
|---|---|---|---|
| 3,810,886 | 5/1974 | Rutner et al. | 260/239.57 |
| 3,855,208 | 12/1974 | Rutner et al. | 260/239.57 |
| 3,855,208 | 12/1974 | Rutner et al. | 260/239.57 |

Primary Examiner—Elbert L. Roberts
Attorney, Agent, or Firm—Donald Brown

[57] ABSTRACT

Compounds of formula (VIII) wherein
$R^1$, $R^2$, $R^3$, $R^4$ and $R^5$ are each selected from hydrogen and an hydroxyl group and at least four are hydrogen;
B is an alkylene chain of from 1 to 4 carbon atoms;
R is selected from hydrogen and an alkyl group of from 1 to 4 carbon atoms;
A is selected from a bond and a straight or branched, optionally substituted alkylene chain of 1 to 6 carbon atoms, and
$X^1$ and $X^2$ are each selected from hydrogen and an iodine radioisotope.

Compounds of this formula are of value as agents for use in the radioimmunoassay of corresponding genins of formula (V) and derivatives thereof. Also provided by the invention are a radioimmunoassay method utilizing compounds of formula (VIII) and a test kit suitable for use in performing the assay.

18 Claims, 12 Drawing Figures

FIG.1

SCHEME 1

(V)

(VI)     $NH_2 \cdot O \cdot B \cdot COOH$ (VII)

(VIII)

(IX)

(X)

BIOLOGICAL REAGENT

This invention relates to reagents for the assay of cardenolides and derivatives thereof in solutions containing them, to the preparation of such reagents, to a method of performing such assays utilizing such reagents, to a test kit suitable for performing such assays, and to a method for making such a test kit.

The present invention relates more particularly to novel reagents for the radioimmunoassay of card-20(22)-enolides having in the 3- position a keto group or a group capable of selective oxidation to a keto group and of derivatives of such cardenolides. The present invention relates especially to reagents for the radioimmunoassay of the 3- glycone derivatives of such cardenolides (cardiac glycosides), and more especially to reagents for the radioimmunoassay of digoxin, digitoxin, gitoxin, periplocin and lanatosides A, B and C. By use of the reagents provided by the present invention these cardenolides and their derivatives may be assayed both in aqueous solution and in urine.

It is known in the art that the technique of radioimmunoassay may be adapted to the assay of cardiac glycosides. In this adapted technique a limiting, fixed quantity of glycoside antiserum, prepared by standard immunological procedures, is allowed to react with, for example, test urine or a standard solution of the glycoside together with a constant amount of the glycoside radioactively labelled in such a manner that antigenic properties of the molecule are substantially unaffected. Following incubation of the mixture, free glycoside is separated from that bound to antibody by any of the available procedures and the radioactivity of one or other of the two fractions is measured in a radioactivity counter. The binding of labelled glycoside is progressively inhibited by increasing amounts of unlabelled glycoside due to competition between the two species for the specific binding sites on the antibody. The concentration of glycoside in the urine under test may readily be determined by reference to a standard curve prepared at the same time.

Because of the cross reactivity exhibited between them in their reaction with antibodies directed against the one or the other, either a glycoside or its aglycone (the genin), wherein there is a hydroxy group in the 3-position, may, when labelled, be used in the assay technique for glycosides described above provided of course that, as indicated above, the introduction of the label leaves the antigenic properties of the molecule substantially unaffected. Thus for the assay of digoxin, digitoxin, gitoxin and periplocin there may be used either labelled glycoside or labelled digoxigenin, digitoxigenin, gitoxigenin and periplogenin respectively. For the assay of lanatosides A, B and C there may be used either the labelled glycoside or the appropriate labelled genin, i.e. digitoxigenin, gitoxigenin and digoxigenin respectively.

One of the assay methods described hitherto in the literature relating to the use of labelled genins involved the tritiated compounds, with the associated disadvantages of low specific radioactivity and the need for measuring samples in a liquid scintillation counter.

In a second literature method, relating specifically to the assay of digitoxin, the labelled compound was a 3-O-succinyl derivative of digitoxigenin prepared by succinylation of the genin and the subsequent introduction into the succinyl moiety of a radioiodine label. A disadvantage of this second approach is the need for succinylation of the genin to be effected under mild conditions, and hence for extended reaction times, if dehydration involving the 14-hydroxy group of the genin is to be avoided. A further disadvantage is that if the approach is applied to genins having more than one esterifiable hydroxy group, for example digoxigenin which has such groups in both the 3- and 12- positions, a mixture of succinates is formed. As the evidence is that, for digoxigenin, an unsubstituted 12-hydroxy group is essential for immunological specificity, it is necessary either for the 12- hydroxy group to be selectively blocked prior to the succinylation step by a substituent that can ultimately be preferentially removed, or for the 3-O-succinyl derivative to be isolated from the 12- and 3, 12-esterified compounds.

It has now been found that novel antigenically satisfactory digoxigenin analogues, having high specific radioactivity and permitting measurement of samples with the more convenient solid crystal scintillation counter, involving none of the synthetic difficulties of the prior art and stable when freeze dried, are prepared by the sequential steps of:

SCHEMES I–X a. Selective oxidation of the 3-hydroxy group of digoxigenin (I) to yield the corresponding ketone, 3-dehydrodigoxigenin (II);

b. Reaction of the ketone (II) with 0-carboxymethylhydroxylamine to yield 3-dehydrodigoxigenin 3-0 -carboxymethyloxime (III);

c. Reaction of the oxime (III) with β-(4-hydroxyphenyl) alanine methyl ester to yield N -(3-dehydrodigoxigenin 3-0-carboxymethyloxime) β-(4-hydroxyphenyl)alanine methyl ester (better named 3-dehydrodigoxigenin 3-0-[α-(methoxycarbonyl)-4-hydroxyphenethylcarbamoylmethyl]oxime. (IV);

d. Iodination of the ester (IV) with $^{125}$I to yield successively the compounds N -(3-dehydrodigoxigenin 3-0-carboxymethyloxime) β-(4-hydroxy-3-[$^{125}$I]iodophenyl)alanine methyl ester (better named 3-dehydrodigoxigenin 3-0-[α-(methoxycarbonyl)-4-hydroxy-3-($^{125}$I)iodophenethylcarbamoylmethyl]oxime; and N -(3-dehydrodigoxigenin 3-0-carboxymethyloxime) β-(4-hydroxy-3,5-di[$^{125}$I]iodophenyl)alanine methyl ester (better named 3-dehydrodigoxigenin 3-0-[α-(methoxycarbonyl)-4-hydroxy-3,5-di($^{125}$I)iodophenethylcarbamoylmethyl]oxime.

Steps (a), (b) and (c) of the above are illustrated in the accompanying Scheme 1 and as will be clear from the foregoing during the iodination step (d) the radioiodine label is introduced successively into the 2- and 6- positions (with respect to the hydroxy group) of the phenol moiety of the ester (IV).

It has been found that the digoxigenin (I) and 3-dihydrodrodigoxigenin (II) may, as appropriate, be replaced by any cardenolide having in the 3-position a keto group or a group capable of selective oxidation to a keto group, and that there may thus be obtained novel antigenically satisfactory, radioiodinated analogues, presenting the advantages indicated above, of the compounds (genins) of formula (V) wherein $R^1$, $R^2$, $R^3$, $R^4$ and $R^5$ are each either hydrogen or an hydroxyl group and at least four of these are hydrogen.

The compounds of formula (V) are detailed in Table 1 overleaf.

Provided that there is present in the starting material of formula (V) no other oxidisable hydroxy group, selective oxidation of the 3-hydroxy group may be effected by catalysis using for example a platinum catalyst, or by the use of an agent such as chromic acid or potassium permanganate; if however there is present one or more additional oxidisable hydroxy groups, as in for example digoxigenin and gitoxigenin which each have one such additional group in respectively the 12- and 16- positions, then catalytic oxidation as indicated above is alone possible.

Table 1

|  | $R^1$ | $R^2$ | $R^3$ | $R^4$ | $R^5$ |
|---|---|---|---|---|---|
| Digoxigenin | H | H | H | OH | H |
| Digitoxigenin | H | H($\beta$-) | H | H | H |
| Gitoxigenin | H | H | H | H | OH |
| Periplogenin | H | OH | H | H | H |
| Uzarigenin * | H | H($\alpha$-) | H | H | H |
| Urezigenin ** | H | H($\alpha$-) | H | H | H |
| Sarmentogenin | H | H | OH | H | H |
| Acovenosigenin | OH | H | H | H | H |

* 3-OH is $\beta$
** 3-OH is $\alpha$

Reaction step (c) may be effected using any procedure known in the art and conveniently by use of dicyclohexylcarbodiimide or by the mixed anhydride method with isobutylchloroformate.

Iodination may be performed by any of the known procedures but is preferably carried out using a modification of the chloramine T procedure standard in the art. Although iodine is introduced into the phenol moiety at either the 2- position or both the 2- and 6- positions with respect to the hydroxy group it has been found that the majority of the labelled ester incorporates only a single iodine atom.

It will be appreciated that in principle any of the radioisotopes of iodine ($^{123}I$, $^{124}I$, $^{125}I$, $^{126}I$, $^{128}I$, $^{129}I$, $^{130}I$, $^{131}I$ and $^{132}I$) may be introduced into the ester (IV) but that, from considerations of availability, half-life and specific activity, $^{125}I$ and $^{131}I$ are preferred and $^{125}I$ most preferred.

It has also been found that the 0-carboxymethylhydroxylamine reagent of step b) above may be replaced by any 0-carboxyalkylhydroxylamine of general formula (VI), wherein B is an alkylene chain. Preferred amongst such compounds however are those wherein B is unbranched, and most preferred are those wherein B has from 1 to 4 carbon atoms such as the methyl compound identified above (B is —CH—).

It has further been found that the $\beta$-(4-hydroxy-phenyl)alanine methyl ester reagent of step (c) above may be replaced by any primary or secondary aminophenol of formula (VII) wherein A is a bond or is a straight or branched, optionally substituted alkylene chain which preferably has from 1 to 6 carbon atoms and R is hydrogen or is an alkyl group of from 1 to 4 carbon atoms. As another preferred feature the hydroxyl group in the compound of formula (VII) is in the 4-position with respect to A. The primary amino compounds (R is hydrogen) are preferred amongst those of formula (VII) however and as examples of particularly suitable primary compounds may be mentioned p-hydroxybenzylamine (A is —CH$_2$- ), $\beta$-(4-hydroxy-phenyl)alanine (A is —CH(COOH)CH$_2$—) and esters of $\beta$-(4-hydroxyphenyl)alanine, for example alkyl esters (A is —CH(COO.ALK)CH$_2$—) where the alkyl group 'ALK' preferably has 1 to 4 carbon atoms such as the methyl ester identified above (ALK is —CH$_3$).

From the foregoing it will be appreciated that the ester (IV) and the iodinated derivatives thereof identified above are but examples of a novel class of compounds of formula (VIII) wherein $R^1$, $R^2$, $R^3$, $R^4$ and $R^5$ are each either hydrogen or an hydroxyl group and at least four are hydrogen;

B is an alkylene chain as defined in formula (VI); R is hydrogen or an alkyl group of from 1 to 4 carbon atoms;

A is a bond or is an alkylene chain as defined in formula (VII); and $X^1$ and $X^2$ are each either an iodine radioisotope or hydrogen.

The iodinated compounds of formula (VIII) may be prepared from the corresponding, non-iodinated esters in the manner described above. The non-iodinated esters may themselves be prepared by the sequential steps of (a) selective oxidation of the appropriate compound of formula (V), (b) reaction of the resulting ketone with the appropriate compound of formula (VI) to yield the oxime; and (c) reaction of the oxime with the appropriate compound of formula (VII), by processes analogous to those described above.

It will be appreciated that the novel compounds of formula (VIII) and the oximes from which they derive may together be represented by formula (IX) wherein $R^1$, $R^2$, $R^3$, $R^4$, $R^5$ and B are as defined in formula (VIII) and Z is an hydroxyl group or a group of formula (X) wherein R, A, $X^1$ and $X^2$ are as defined in formula (VIII).

Preferred compounds of formulae (VIII) and (IX) are those wherein $R^1$ and $R^3$ are both hydrogen.

The assay of a compound of formula (V) (genin) or of a 3-glycone derivative (glycoside) thereof may be conveniently effected by use of a test kit comprising at least four vessels, a first vessel containing a buffer solution, a second vessel containing a mixture of (a) an antiserum raised in a species of mammal or bird reactive against the genin or glycoside to be assayed, and (b) an antiserum raised in a second species of mammal or bird reactive against the immunoglobulins of the first species, a third vessel containing a solution of a compound of formula (VIII) corresponding to the genin or glycoside to be assayed and in which at least one of $X^1$ and $X^2$ is an iodine radioisotope, and a fourth vessel containing a standard solution of the genin or glycoside in serum from a species of mammal or bird other than the species in which the antiserum reactive against the genin or glycoside was raised.

Optionally the contents of one or more of the vessels are in the freeze dried state, and conveniently the kit comprises in addition to the first, second and third vessels identified above a plurality of vessels each containing a standard solution of the genin or glycoside in serum from a species of mammal or bird other than the species in which the antiserum reactive against the genin or glycoside was raised, the standard solutions being of different concentrations the one from the other.

From the discussion hereinabove of the cross-reactivity of glycosides and their genins it will be appreciated that these species are equivalent as contents of the fourth vessel of the test kit as above described.

Among those glycosides particularly conveniently assayed by the use of a test kit as hereinabove described are digoxin, digitoxin, gitoxin, periplocin, lanatoside A, lanatoside B and lanatoside C, and test kits suitable for the assay of these glycosides are particularly valuable among those hereinabove described.

In various aspects therefore there are provided by the present invention:

the compounds of formula (IX), and methods for their preparation as herein described;

a method for the radioimmunoassay of a genin of formula (V) or a 3-glycone derivative (glycoside) thereof comprising in sequence the steps of (a) reacting (i) a genin of formula (V) or a glycoside thereof together with (ii) an antiserum to the genin or glycoside and (iii) a radioiodinated compound of formula (VIII) corresponding to the genin or glycoside, (b) separating the antibody-bound reagent fraction from the nonantibody-bound fraction, and (c) measuring the radioactivity of one of the said fractions;

a test kit, as herein described, suitable for use in the radioimmunoassay of a genin of formula (V) or a 3-glycone derivative thereof; and a method of making a test kit, as herein described, suitable for use in the radioimmunoassay of a genin of formula (V) or a 3-glycone derivative thereof comprising the assembling in kit form of the vessels as described.

The following Examples serve to describe the present invention, by way of illustration only, and do not in any way limit the invention described above. All temperatures are in degrees Celsius. In Examples 4 and 5 the reagent identified as "radioactive digoxlgenin" was the product of the process of Example 3.

EXAMPLE 1

Preparation of 3-dehydrodigoxigenin 3-0-carboxymethyloxime a. 3 - Dehydrodigoxigenin Platinum oxide (Adams' catalyst) (500 mg.) was suspended in water (50 ml.) and a continuous stream of hydrogen passed for 1 hour. The hydrogen was displaced by nitrogen and digoxigenin (2.0 g.), in acetone (200 ml.) and water (50 ml.), added. A continuous stream of oxygen was passed through the mixture for 18 hours. The catalyst was removed by filtration, washed with acetone, the washings added to the filtrate and the filtrate concentrated in vacuo. The residue was dissolved in chloroform, washed with water and the solution dried (magnesium sulphate). Evaporation of the solvent in vacuo gave a gum which crystallised from acetone/ether. The 3-dehydrodigoxigenin melted at 251.2°C. and had $[\alpha] D^{25} + 39.1°$ (c = 0.48 in methanol).

b. 3-Dehydrodigoxigenin 3-0-carboxymethyloxime

3- Dehydrodigoxigenin (1.68 g.) was dissolved in methanol (50 ml.) and 0- carboxymethylhydroxylamine hemihydrochloride (0.48g.) and N - sodium hydroxide (6.59 ml.) added. The mixture was refluxed for 1 hour, concentrated in vacuo, water (75 ml.) added and the mixture then extracted with ether (50 ml.). The aqueous phase was acidified to Congo red with N-hydrochloric acid and the resulting precipitate filtered, washed with water, and dried in vacuo. By crystallisation from aqueous alcohol, the product was isolated as small, colourless prisms, m.p. 241.1°C(decomp.), solvated with ethanol.

Analysis for $C_{25} H_{35} NO_7 . C_2H_5 OH$. Calculated: C, 63.9; H, 8.1; N, 2.8%. Found: C, 63.8;H, 8.0; N, 2.9%.

EXAMPLE 2

Preparation of N -(3-dehydrodigoxigenin 3-0-carboxymethyloxime) β-(4-hydroxyphenyl) alanine methyl ester L-Tyrosine methyl ester* hydrochloride (231.5mg.) and 3-dehydrodigoxigenin 3-0-carboxymethyloxime (461 mg.) were dissolved in a mixture of methylene dichloride (7 ml.) and dimethylformamide (3 ml.). The solution was cooled to 0°C. and dicyclohexylcarbodiimide (206 mg.) added. After stirring the mixture at 0°C. for 24 hours the precipitated dicyclohexylurea was filtered, washed with cold methylene dichloride (5 ml.), the washings added to the filtrate and the filtrate concentrated in vacuo. The residue was dissolved in chloroform (50 ml.) and washed sucessively with 10 ml. portions of water, 0.5N- hydrochloric acid, N-sodium carbonate and water. After drying with magnesium sulphate, the chloroform was evaporated in vacuo. The residue was dissolved in ethyl acetate (5 ml.) and the filtered solution added to light petroleum (100 ml.) The precipitate was filtered, washed with light petroleum and dried.

The product was purified by chromatography on silica gel with the solvent mixture methanol: chloroform (2:8 v/v), monitoring the eluate by means of an ultraviolet absorptiometer. The fractions absorbing at 254 mμ were combined and concentrated in vacuo to give a white amorphous solid. The product was homogeneous on thin layer chromatography (silica gel plates; methyl ethyl ketone $R_f$ 0.48; methanol: chloroform (2:8 v/v)$R_f$ 0.50) and gave positive reactions with Pauly's reagent (for tyrosine) and Raymond's reagent (for cardenolides). Analysis by nuclear magnetic resonance spectroscopy indicated that the ratio of phenol to cardenolide was 1:1.

* Synonym: β-(4-hydroxyphenyl)alanine methyl ester.

Analytical data for N -(3-dehydrodigoxigenin 3-0-carboxymethyloxime) β-(4-hydroxyphenyl)alanine methyl ester.

a. Elemental analysis $C_{35}H_{46}N_2O_9$ Requires - C, 65.8; H, 7.3; N, 4.4%. Found - C, 65.6; H, 7.6; N, 4.6%.

b. Infrared spectroscopy

Figure 1:
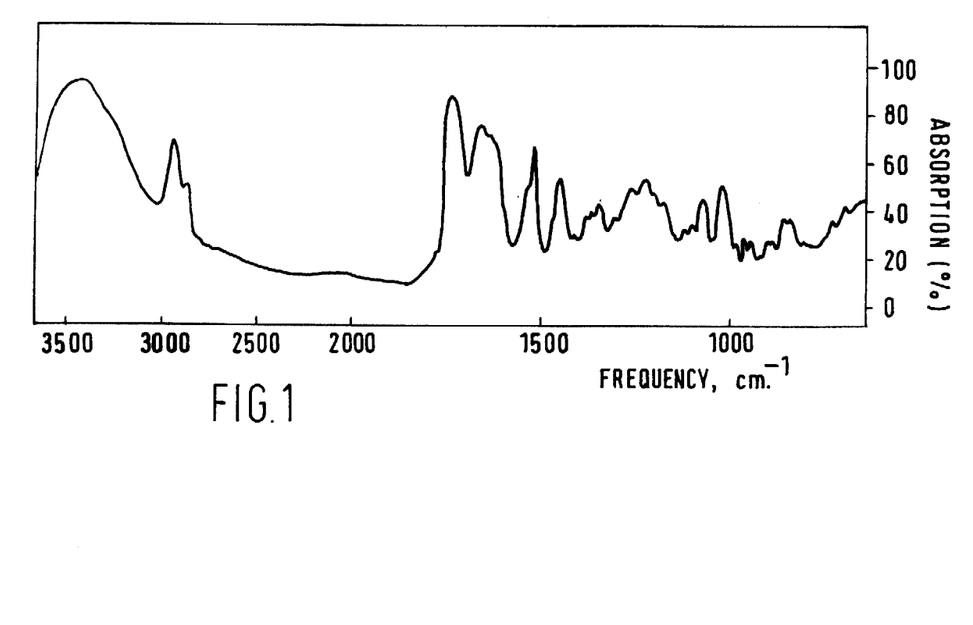

The infrared absorption spectrum of the compound (1.28 mg.) in a potassium bromide disc (16 mm. diameter) is shown in the accompanying FIG. 1. The main bands of interest are as follows:

| $cm^{-1}$ | |
|---|---|
| 844 | } phenyl |
| 864 | |
| 1023 | } alcoholic C—OH |
| 1073 | |
| 1224 | } phenolic C—OH |
| 1257 | |
| 1346 | |
| 1445 | |
| 1515 | } phenyl |
| 1530 | amide |
| 1655 | amide |

-continued $$\left.\begin{array}{l}1734\\1775\end{array}\right\} \text{lactone and } -COOCH_3$$

c. Nuclear magnetic resonance spectroscopy

The N.M.R. spectrum was recorded at 100 MHz as a hexadeutero-dimethylsulphoxide solution. Chemical shift, coupling and integration supported the proposed structure. No impurities were observed.

| Protons | Observed Chemical Shifts (ppm) | Characteristics |
|---|---|---|
| Phenolic | 6.89 | doublet |
| Phenolic | 6.55 | doublet |
| Lactone | 5.75 | singlet |
| Methylester | 3.54 | singlet |
| Tyrosine $\beta$-$CH_2$* | 2.75 | doublet |
| Angular $CH_3$ | 0.80 and 0.92 | singlets | ppm = parts per million (referred to hexamethyldisiloxane internal standard)
*Synonym: $\beta$-(4-hydroxyphenyl)alanine

EXAMPLE 3

Iodination of N -(3-dehydrodigoxigenin 3-0-carboxymethyloxime) $\beta$-(4-hydroxyphenyl) alanine methyl ester To sodium iodide ($^{125}$I, 2 mc) in sodium phosphate buffer (0.5 M, 25μl., pH 7.5) was added the ester (2.5μg.) in 10% aqueous ethanol (12.5μl.), and "chloramine T" ((N-chloro-p-toluenesulphonamido) sodium) (10μg.) in the same phosphate buffer (20 μl.). After stirring the mixture for 30 seconds, using a miniature magnetic stirrer, the reaction was stopped by the addition of sodium metabisulphite (100 μg.) in phosphate buffer as before (20μl.). Dimethylformamide (0.5 ml.) and deionised water (0.3 ml.) were then added and the mixture transferred to a column (25 × 15 mm) of Amberlite IRA 4 0 (Cl form) prewashed with deionised water. The column was eluted with TRIS (tris(hydroxymethyl)aminomethane)— hydrochloric acid buffer (composition as below) (pH 8.5) : 1 ml. fractions were collected, the bulk of the iodinated derivative appearing in the third to sixth portions.

Typical results show a 70 – 85% incorporation of the iodine into the ester.

The buffer used to elute the column had the following composition:

| TRIS | to 0.1M |
|---|---|
| Sodium chloride | to 1.0M |
| Tween 20 | to 0.5% w/w |
| Sodium azide | to 0.05% w/w |
| Concentrated hydrochloric acid | to pH 8.5 |

EXAMPLE 4

Digoxin Radioimmunoassay

The assay was carried out in polystyrene test tubes (8 × 63 mm) using the following reagents:

1. Diluent buffer. Phosphate-saline buffer (pH 7.4) having the composition detailed below was used for diluting all reagents and samples.

1 liter of the buffer contained:

| Sodium dihydrogen phosphate dihydrate | 6.24g. |
|---|---|
| Disodium ethylenediamine tetraacetic acid | 3.72g |
| Bovine serum albumin | 5.0g |
| Sodium azide | 1.0g |
| Sodium chloride | 9.0g |

After making up to 900ml. with deionised water the pH was adjusted to 7.4 with 5N - sodium hydroxide and water added to 1 liter.

2. Anti-digoxin serum (rabbit) at a dilution which bound approximately 50 percent of the radioactive digoxigenin added, in the absence of unlabelled digoxin.

3. Radioactive digoxigenin: digoxigenin-tyrosine methyl ester labelled with $^{125}$I, working strength solution 1 ng/ml.

4. Standard digoxin. Stock solution in phosphate-saline buffer as above of 100 ng/ml diluted 1:12.5 to give first working strength dilution of 8 ng/ml, then doubling dilutions to give 4.0, 2.0, 1.0, 0.5 and 0.25 ng/ml.

5. Normal horse serum
6. Normal rabbit serum, diluted 1:500
7. Precipitating serum: Donkey antiserum to rabbit gamma-globulin, diluted 1:20.

Procedure

Test tubes were set up in triplicate for the blank (to which no antiserum was added), the zero standard, digoxin standards and urine samples. 0.4 ml. Of normal rabbit serum (1:500 dilution) was added to each tube followed by 0.1 ml volumes of standard digoxin solution, normal horse serum (to control and standard tubes only); test urine, radioactive digoxigenin solution and antidigoxin serum. 0.1 ml Radio-active digoxigenin solution alone was pipetted into polystyrene tubes as a sample of the total radioactivity added. The contents of the tubes were mixed on a vortex mixer and the tubes incubated for 30 minutes at room temperature. 0.1 ml Precipitating serum (1:20 dilution) was then added, the contents of the tubes mixed and the tubes stood overnight at 4°C. After centrifugation for 20 minutes at 2,000 g, aspiration of the supernatant and addition of 1 ml wash buffer (composition identical with that of the diluent buffer) was followed by further centrifugation and aspiration. The radioactivity in the antibody-bound fraction was measured in a well-type scintillation counter.

Prior to assay the test urine samples were diluted with deionised water, in one instance to give a 1:40 dilution and in a second instance a 1:10 dilution. The concentration of digoxin in the diluted urine was determined by reference to a curve prepared from the results obtained with the standard digoxin solutions and the concentration of digoxin in the undiluted urine then calculated.

EXAMPLE 5

Digoxin Radioimmunoassay

A further assay was carried out in glass test tubes using the following reagents:

1. Wash Buffer: phosphate-saline buffer (pH 7.4) prepared as follows:

| | |
|---|---|
| Sodium chloride | 9.0g. |
| Sodium dihydrogen phosphate, dihydrate | 6.2g |
| Bovine albumin powder | 5.0g. |
| Sodium azide | 1.0g. |
| Deionised water | to 900 ml. |
| pH adjusted to 7.4 with sodium hydroxide | |
| Deionised water | to 1 liter |

2. Digoxin Binding Reagent: a mixture of (a) rabbit anti-digoxin serum, and (b) donkey antiserum to rabbit gamma-globulin, the reagent reconstituted as required from freeze dried material by addition of deionized water.

3. Radioactive Digoxigenin: digoxigenin-tyrosine methyl ester labelled with $^{125}I$, working strength solution of 1 ng/ml. in buffer as in 1. above, reconstituted as required from freeze dried material by addition of deionized water.

4. Standard Digoxin: solutions in bovine serum at concentrations of zero, 0.5, 1.0, 2.0, 3.0, 4.0 and 6.0 ng/ml., reconstituted as required from freeze dried material by addition of deionized water.

Procedure

Test tubes were set up in duplicate with the composition as indicated below, the reagents being added in the order shown:

| | Zero and other standards | Test urine |
|---|---|---|
| Standard digoxin solution (ml.) | 0.1 | — |
| Test urine (diluted — see below) (ml.) | — | 0.1 |
| Radioactive digoxigenin solution (ml.) | 0.1 | 0.1 |
| Digoxin binding reagent (ml.) | 0.1 | 0.1 |

In addition, 0.1 ml of radioactive digoxigenin solution alone was pipetted into duplicate tubes as a sample of the total radioactivity added.

After addition of the last reagent the contents of each tube were mixed using a vortex mixer and the tubes stood at room temperature for 1½ hours. At the end of this period wash buffer (1 ml.) was added to each tube (excluding those containing radioactive digoxigenin solution alone) and the tubes and contents centrifuged at 2000g for 20 minutes. The supernatant was then discarded and the radioactivity of the precipitate (the antibody-bound fraction) measured using a well-type crystal scintillation counter.

Figure 2:
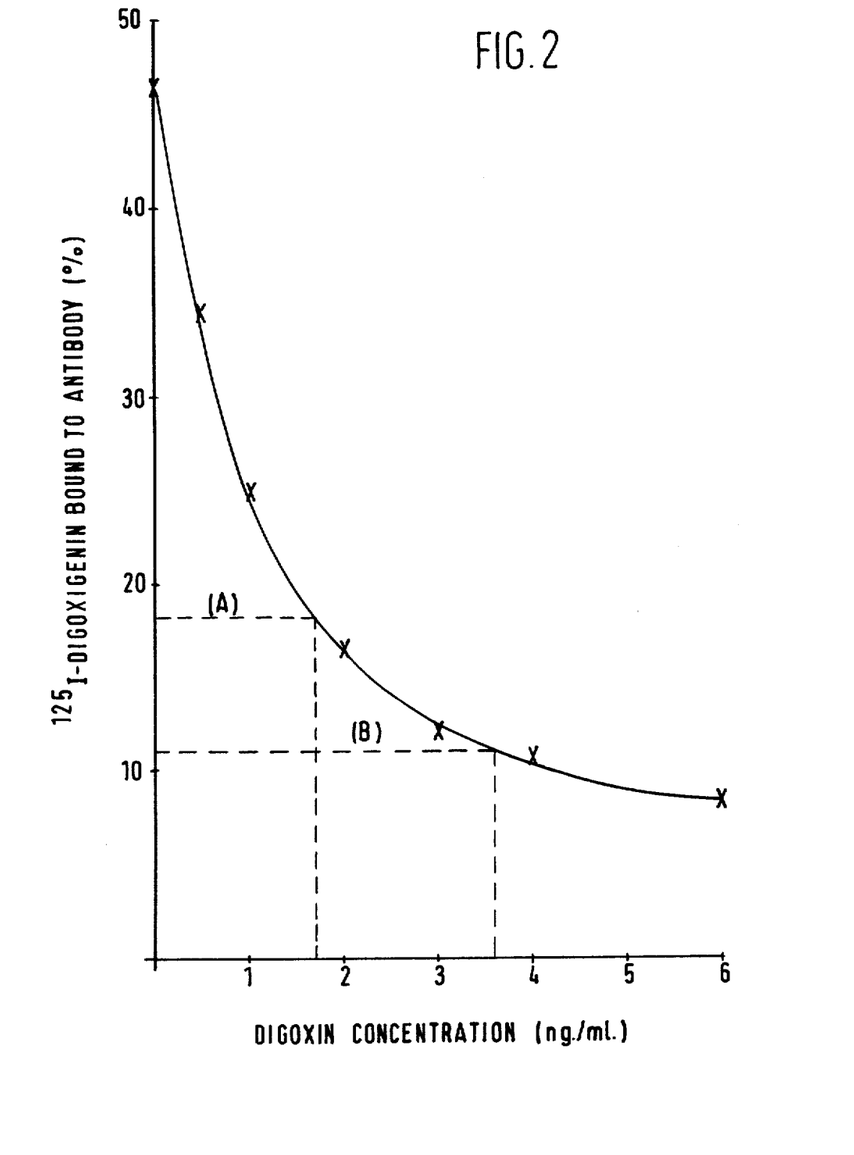

Using this technique the concentration of digoxin in two test samples of urine was determined by reference to a curve prepared from the results obtained with the standard digoxin solutions, as shown in the accompanying FIG. 2. Prior to assay sample (A) was diluted 1:40 and sample (B) 1:10, in each instance using deionised water. The concentration of digoxin in sample (A) (diluted) was determined as 1.7 ng./ml. and that in sample (B) (diluted) as 3.6 ng./ml.: hence the concentrations in the undiluted samples were 68ng./ml. and 36 ng./ml. respectively.

What we claim is:
1. A compound of formula (VIII)

wherein $R^1$, $R^2$, $R^3$, $R^4$ and $R^5$ are each selected from hydrogen and an hydroxyl group and at least four are hydrogen;

B is an alkylene chain of from 1 to 4 carbon atoms;

R is selected from hydrogen and an alkyl group of from 1 to 4 carbon atoms;

A is selected from a bond and a straight or branched, alkylene chain of from 1 to 6 carbon atoms which may be substituted by a carboxyl or carboalkoxy group wherein the alkyl thereof has 1 to 4 carbon atoms; and $X^1$ and $X^2$ are each selected from hydrogen and an iodine radioisotope.

2. A compound according to claim 1 wherein at least one of $X^1$ and $X^2$ is an iodine radioisotope.

3. A compound according to claim 1 wherein $X^1$ and $X^2$ are both hydrogen.

4. 3-dehydrodigoxigenin 3-0-oxime.

5. 3-dehydrodigoxigenin 3-0-oxime.

6. 3-dehydrodigoxigenin 3-0-oxime.

7. The compound of claim 1 where A is a bond or alkylene of from 1 to 6 carbon atoms.

8. The compound of claim 7 wherein at least one of $X^1$ and $X^2$ is an iodine radioisotope.

9. The compound of claim 7 wherein both $X^1$ and $X^2$ are hydrogen.

10. The compound of claim 1 where A is $—CH_2—$, $—CH(COOH)CH_2—$ or $—CH(COO.ALK)CH_2—$ and ALK has from 1 to 4 carbon atoms.

11. The compound of claim 10 wherein ALK is $—CH_3$.

12. A compound as claimed in claim 2 wherein the iodine radioisotope is selected from $^{125}I$ and $^{131}I$.

13. A compound as claimed in claim 1 wherein B is $—CH_2—$.

14. A compound as claimed in claim 1 wherein the —OH group in the terminal phenyl group is in the 4-position with respect to A.

15. A compound as claimed in claim 1 wherein $R^1$ and $R^3$ are both hydrogen.

16. A compound as claimed in claim 1 wherein R is hydrogen.

17. A compound as claimed in claim 16 wherein A is selected from $—CH_2—$, $—CH(COOH)CH_2—$, and $—CH(COO.ALK)CH_2—$, where ALK is an alkyl group of 1 to 4 carbon atoms.

18. A compound as claimed in claim 17 wherein A is $—CH(COO.CH_3)CH_2—$.

* * * * *